(12) United States Patent
Luecke et al.

(10) Patent No.: US 8,085,896 B2
(45) Date of Patent: *Dec. 27, 2011

(54) RIGID COMPUTED TOMOGRAPHY ROTOR AND METHOD FOR THE MANUFACTURE THEREOF

(75) Inventors: Daniela Luecke, Germering (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 87 days.

This patent is subject to a terminal disclaimer.

(21) Appl. No.: 12/533,198

(22) Filed: Jul. 31, 2009

(65) Prior Publication Data

US 2010/0027757 A1 Feb. 4, 2010

(30) Foreign Application Priority Data

Aug. 1, 2008 (DE) .......................... 10 2008 036 014

(51) Int. Cl.
*H05G 1/60* (2006.01)
*H05G 1/02* (2006.01)

(52) U.S. Cl. ................. 378/4; 378/15; 378/197

(58) Field of Classification Search .............. 378/4, 15, 378/197

See application file for complete search history.

(56) References Cited

U.S. PATENT DOCUMENTS

| 5,654,094 A * | 8/1997 | Patel et al. .................... 428/367 |
| 2006/0018437 A1 | 1/2006 | Russinger |
| 2007/0064863 A1 | 3/2007 | Buttner et al. |

FOREIGN PATENT DOCUMENTS

| DE | 42 14 858 C1 | 2/1994 |
| DE | 20 2006 004 118 U1 | 8/2007 |

OTHER PUBLICATIONS

U.S. Appl. No. 12/533,228, filed Jul. 31, 2009.
U.S. Appl. No. 12/533,213, filed Jul. 31, 2009.
U.S. Appl. No. 12/533,184, filed Jul. 31, 2009.
U.S. Appl. No. 12/533,148, filed Jul. 31, 2009.

* cited by examiner

*Primary Examiner* — Irakli Kiknadze
(74) *Attorney, Agent, or Firm* — Schiff Hardin LLP

(57) ABSTRACT

A rotor for a gantry of a computed tomography apparatus, as well as a manufacturing method for such a rotor. The rotor according to the invention is produced at least in segments from a composite material with polymer matrix that is reinforced with fibers. The rotor thus has a high strength and rigidity, such that the deformation limits to achieve a sufficiently good image quality with simultaneously low structural volume and low weight are not exceeded, even at high rotation speeds.

25 Claims, 3 Drawing Sheets

RIGID COMPUTED TOMOGRAPHY ROTOR AND METHOD FOR THE MANUFACTURE THEREOF

RELATED APPLICATION

The subject matter of the present application is related to the subject matter of an application filed simultaneously with the present application, having Ser. No. 12/533,213, entitled Computed Tomography Rotor Rigidified By A Metal Matrix Material.

BACKGROUND OF THE INVENTION

1. Field of the Invention

The present invention concerns a rotor for a gantry of a computed tomography apparatus, as well as a manufacturing method for such a rotor.

2. Description of the Prior Art

Computed tomography apparatuses enable the reconstruction of three-dimensional slice or volume images of an examination region for diagnostic purposes. The reconstruction of an image ensues on the basis of projections of an examination region that are acquired by irradiating a subject with an x-ray fan beam from different projection directions by rotation of an acquisition device so that measurement data are acquired for parallel projections in an angle range of at least 180 degrees plus the fan angle for reconstruction of an image. To achieve the rotation of the data acquisition device, the computed tomography apparatus has a gantry that has a stationary frame and a rotor arranged such that it can rotate by means of a rotating bearing device. The image data acquisition device is mounted on the rotor. The rotor has been produced conventionally as a cast part made of an aluminum alloy AlZn10SiMg and has a rotor wall in the form of an annular disc and a retention ring running along its outer periphery for mounting the components of the acquisition device. The wall thicknesses of such rotors vary between 15 and 20 mm.

To avoid movement artifacts in the reconstructed image that can arise due to patient or organ movements, it is sought to select the time window for acquisition of the projections required for reconstruction to be as small as possible by the use of high rotation speeds. Rotation speeds of 210 R/min are achieved in current computed tomography apparatuses. In the future the rotation speeds are expected to be increased to at least 300 R/min.

Due to a combination of high rotation speed, large rotation radius and high rotation mass, the rotor represents a highly mechanically stressed component that, in addition to accommodating the stresses that are incurred, must also reliably maintain the positions of x-ray tubes and detectors, since position shifts of the components of more than 0.15 mm can lead to a significant degradation of the image quality.

Significant primary requirements for the rotor of a gantry are accordingly not only a high strength to transfer the forces, but also a high rigidity in order to keep deformations of the rotor (and thus the position shifts of the components of the acquisition device) below the allowable limits, given a simultaneously low weight.

An additional thickening of the existing design would be necessary in order to achieve rotation speeds of 300 R/min and more while keeping the same material. The consequence would be a weight increase of the rotor. Components to drive the rotor and the stationary part of the gantry would thereby also have to be adapted to the greater weight. This approach also has the disadvantage of causing a weight and volume increase of the entire gantry.

SUMMARY OF THE INVENTION

It is therefore an object of the present invention to provide a rotor of a gantry of a computed tomography apparatus with a greater rigidity and a greater strength such that high rotation speeds of the rotor do not lead to a position shift of the components of the acquisition system that negatively affects the image quality. Another object of the invention is to provide a method for manufacturing such a rotor.

According to the invention, the rotor for a gantry of a computed tomography apparatus is characterized by the rotor being formed, at least in segments, of a fiber-reinforced composite material with a polymer matrix.

Fiber-reinforced composite materials with a polymer matrix have high specific strength properties and rigidity properties so that the deformation of the rotor is significantly less in comparison to a rotor produced from an aluminum alloy, even given high rotation speeds of 300 R/min and a simultaneously small structural volume. The deformation limits to achieve a sufficiently good image quality are not exceeded, even at high rotation speeds. The use of a fiber-reinforced polymer matrix is additionally also achieves a weight saving, which reduces the costs for transport, for example. Moreover, the drive can also be dimensioned smaller due to the lower rotation mass, which likewise leads to a cost saving.

The fibers used for reinforcement are advantageously carbon fibers, which have a low weight and simultaneously a high strength. The fibers can be industrially manufactured from carbon-containing starting materials and can be processed further into semi-finished fiber products by the use of textile techniques.

The rotor has a particularly high strength and rigidity when the fibers are produced from carbon nanotubes. Carbon nanotubes have over 40% greater rigidity and over 600% greater strength, such that the structural volume and the weight of the rotor can be further minimized with the use of a fiber produced on the basis of this material.

In an embodiment of the invention, the fibers are essentially aligned unidirectionally, at least per segment, in the direction of force paths arising upon rotation of the rotor. In particular, regions of the rotor in which forces are present with a preferred direction can be stabilized particularly well by the introduced fibers. Spatial force paths and the alignment of the fibers associated with the paths can be determined experimentally or numerically, using corresponding mathematical models in the form of a simulation.

In an embodiment of the invention, a continuous fiber is used. As used herein, a "continuous fiber" is a fiber that is longer than 5 cm. Continuous fibers in a simple form can easily be processed further into flat or three-dimensional textiles by appropriate textile techniques such as weaving, braiding or knitting. Complex force distributions in the rotor can be thus formed by correspondingly produced textiles. The fiber used for reinforcement in the rotor has a textile structure, at least per segment.

In regions without a preferred direction of the arising forces, it is appropriate for the fibers to form a layer structure, at least per segment.

A particularly high strength of the rotor is furthermore achieved when the polymer matrix is an epoxy matrix. The curing of the resin ensues in a few minutes or hours by the addition of an accelerator, such that the manufacturing time is also decreased to a significant degree by the use of epoxy resin.

In another embodiment of the invention, the rotor has a rotor wall in the form of a ring rim and a peripheral retention ring provided on the outer or inner circumference of this rotor wall. The retention ring serves for the mounting of components of the image data acquisition device and a rotation bearing device.

The fibers of the composite material are advantageously oriented radially in the rotor wall, thus in the direction of the centrifugal forces that arise upon rotation relative to the rotor wall center point.

The region between rotor wall and retention ring has a particularly high rigidity when the fibers are directed from the rotor wall to the retention ring, and in the retention ring are oriented parallel to the rotation axis of the rotor.

An additional stabilization of the rotor is achieved when the fibers are additionally oriented in the circumferential direction of the rotor wall and/or of the retention ring.

Since the fibers can be damaged by machine processing of the composite material, and thus the strength and rigidity of the rotor can be negatively affected, in an embodiment of the invention retention elements which serve for the mounting of components of the data acquisition device, are integrated into the rotor during manufacture of the rotor.

The retention elements are advantageously produced from a metal (advantageously from aluminum or an aluminum alloy) so that machine processing (to introduce threads, for example) is easily done.

The rotor is advantageously thickened with additional fibers in regions of the retention elements so that the rotor is locally reinforced in the region of the established spot connections with the components.

The rotor wall is advantageously provided with ribs, whereby the ribs are connected with the retention ring. The rigidity of the rotor can be additionally improved with these.

The rotor wall, the retention ring and the ribs are preferably produced as one part. It would naturally also be conceivable for individual parts to be initially manufactured separately and subsequently joined, for example by means of wet lamination. The rotor wall, the retention ring and the ribs could also be glued to one another.

An additional reinforcement can be achieved by, in addition to the fibers, also integrating sandwich elements into the composite material. The sandwich elements are advantageously composed of multiple layers with materials of different density. The degree of rigidity and the degree of strength can be adapted to the local existing requirements of the rotor by a suitable selection of the material combination.

According to the invention, such a rotor can be produced by a method that includes the following features:

a) the fibers are inserted into a work piece, b) the polymer matrix is subsequently injected into the work piece via at least one opening, wherein venting takes place via at least one additional opening in the work piece, and c) a curing ensues via heating of the composite material.

The heating of the composite material is advantageously implemented by means of a heating element integrated into the work piece. Alternatively, microwave technology can be used to heat the composite material.

DESCRIPTION OF THE PREFERRED EMBODIMENTS

Figure 1:
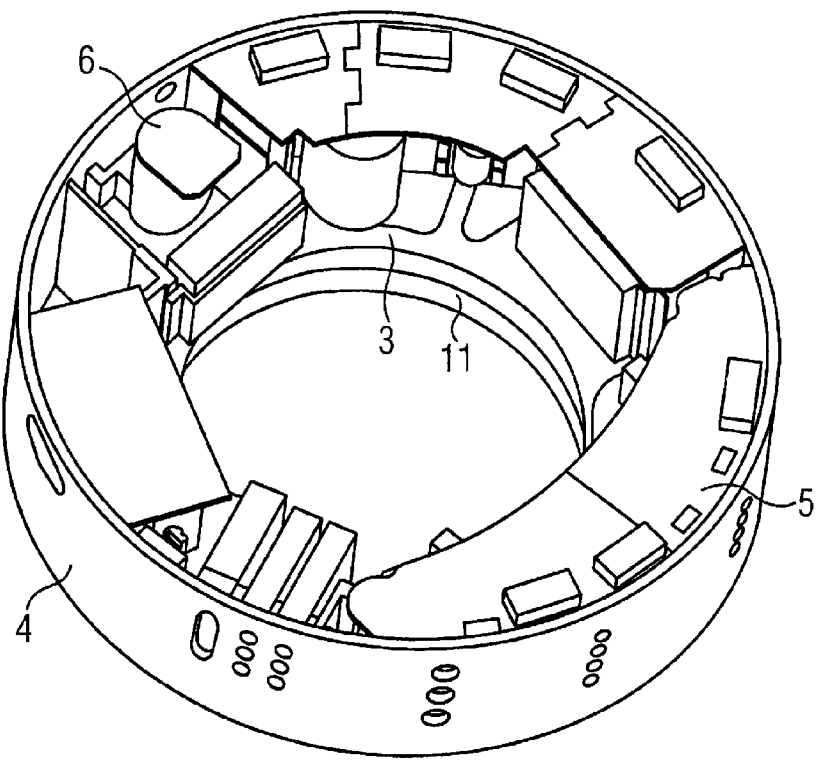
FIG. 1 is a first perspective view of a rotor for a gantry of a computed tomography apparatus with components of an acquisition device.
Figure 2:
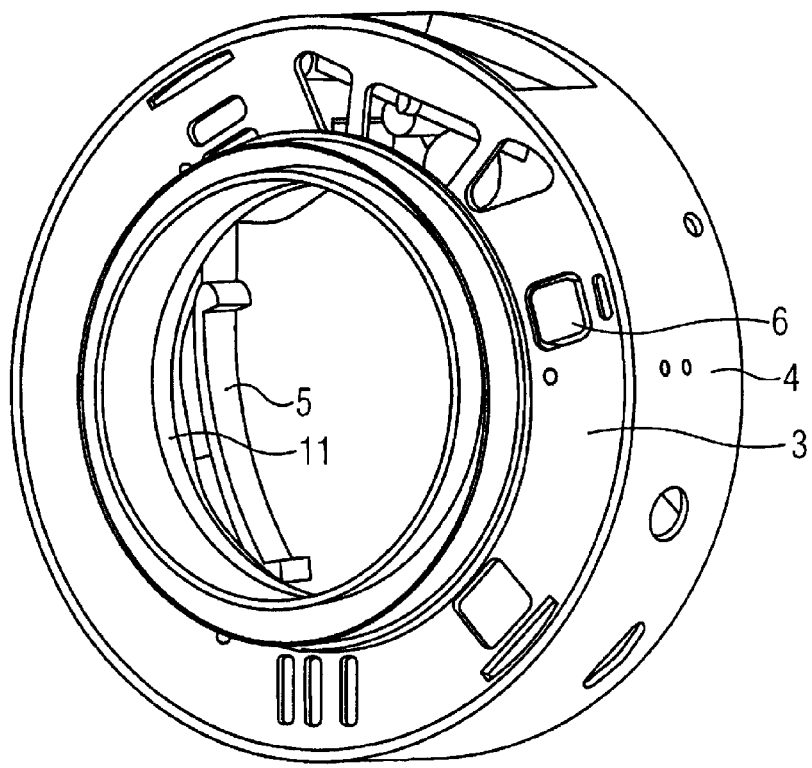
FIG. 2 is a second perspective view of the rotor for a gantry of a computed tomography apparatus with components of an acquisition device.

Two different perspective views of a rotor 1 for a gantry of a computed tomography apparatus shown according to the prior art are shown in FIG. 1 and FIG. 2. The rotor 1 has a rotor wall 3 in the form of a ring rim and a retention ring 4 running on the outer circumference of the rotor wall 3 for the mounting of components 5, 6 of an acquisition device. The acquisition device essentially includes an x-ray radiator in the form of an x-ray tube 6 and a detector 5 arranged opposite the radiator. Moreover, the rotor wall 3 has on its inner circumference components of a rotation bearing device 11 that interact with correspondingly arranged components of a rotation bearing device on a stationary part of the gantry, so that the rotor 1 is mounted so that it can rotate. The rotation speeds of the rotor 1 are presently approximately 210 R/min and should in the future be increased to at least 300 R/min. The rotor 1 represents a highly stressed structural part due to the combination of high rotation speed, large rotation radius and high rotation mass of the components 5, 6 of the acquisition device that are arranged on the retention ring 4. The rotor 1 thus must not only have a high strength to accommodate the stresses occurring during a rotation movement of the rotor 1, but also it must be ensured that the positions of x-ray tube 6 and detector 5 do not significantly change in relation to the scan plane. A position shift of over 0.15 mm would already lead to a degradation of the image quality since the projection conditions forming the basis of the reconstruction of an image are not maintained.

Figure 3:
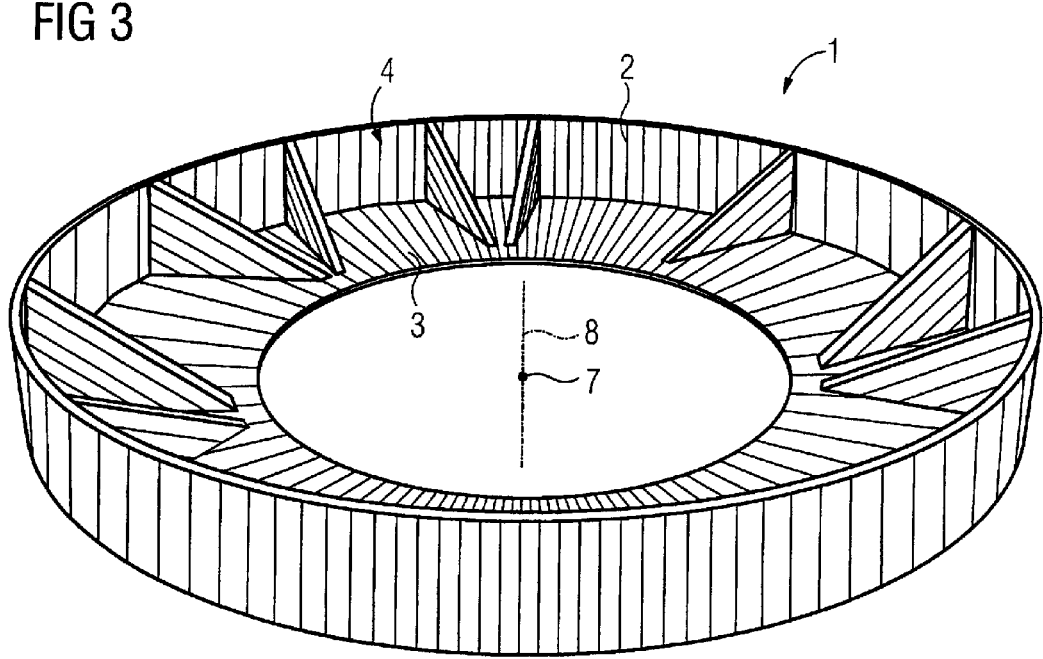
FIG. 3 is a perspective view of a rotor for a gantry with a fiber-reinforced composite material with polymer matrix.

FIG. 3 shows a rotor 1 according to the invention in a perspective view. In order to ensure a high rigidity and strength of the rotor 1 given a simultaneously low structural volume and low weight, the rotor 1 is produced from a composite material reinforced with fibers 2, with a polymer matrix. It is thus possible to operate a computed tomography apparatus even at very high rotation speeds of the rotor 1 without negatively affecting the image quality. Moreover, due to the weight saving, the drive of the rotor 1 does not need to be dimensioned to be stronger. The manufacture of the fiber-reinforced polymer matrix is possible by means of numerous different production methods. The oldest and simplest form is thereby wet lamination with subsequent heat curing. The reinforcement textiles that are produced from long fibers are initially placed in a predefined form. A duroplastic resin system is subsequently applied with a brush. For the curing the laminate is wrapped with a vacuum film (an autoclave technique). With this technique it is possible to design arbitrarily shaped structural parts.

Fibers 2 in the form of carbon fibers are used as a reinforcement material. Carbon fibers are simple to produce and can be processed further in a simple manner into two- or three-dimensional textiles. A particularly high rigidity and strength of the fibers is achieved when the fibers are produced from carbon nanotubes (CNT). Their properties approach the theoretical properties of carbon fibers. In comparison to carbon fibers, a rigidity that is greater by 40% and a strength that is greater by 600% is achieved with the carbon nanotubes in comparison to the carbon fibers, together with an elongation at fracture that is 10 times greater.

FIG. 3 shows the curve of the fibers 2 within the polymer matrix. The fibers 2 thereby run essentially unidirectionally (at least per segment) in the direction of force paths arising upon rotation of the rotor 1. The fibers 2 are oriented radially outwardly toward the rotor wall and point in the direction of the centrifugal forces. The fibers 2 are directed from the rotor wall 3 to the retention ring 4 and in the retention ring 4 run parallel to the rotation axis 8 of the rotor 1. It would likewise be suitable to reinforce the rotor 1 with fibers 2 that are additionally oriented in the circumferential direction of the rotor wall 3. Ribs 10 that additionally increase the rigidity of the rotor 1 are additionally arranged between the rotor wall 3 and the retention ring 4. Rotor wall 3, retention ring 2 and ribs 10 are preferably produced from a single piece. It is also possible to initially manufacture the rotor wall 3, the retention ring 4 and the ribs 10 separately and to subsequently glue them to one another.

The fibers 2 are advantageously continuous fibers, i.e. produced from fibers 2 that are longer than 5 cm. These fibers 2 can be woven, knit or spun into two- or three-dimensional textiles in a simple manner. In this way it can be allowed for that very complex force paths along which the fibers 2 are to be aligned arise within the rotor 1.

Depending on local load, fibers 2 can be aligned unidirectionally or form a textile or layer structure.

An epoxy matrix is normally used as a polymer matrix. Epoxy resin is an easily cured material that can cure within a few seconds or hours upon the addition of an accelerator. The manufacturing times of a rotor 1 are significantly decreased in this way. For an additional local reinforcement structures known as "sandwich cores" can be introduced into the polymer matrix in addition to the fibers 2. The sandwich cores are composed of multiple layers that are constructed from materials of different density and are glued with one another. For example, aluminum plates can be glued with plastic cores. A local stabilization of the rotor 1 can ensue in a targeted manner in this way.

Figure 4:
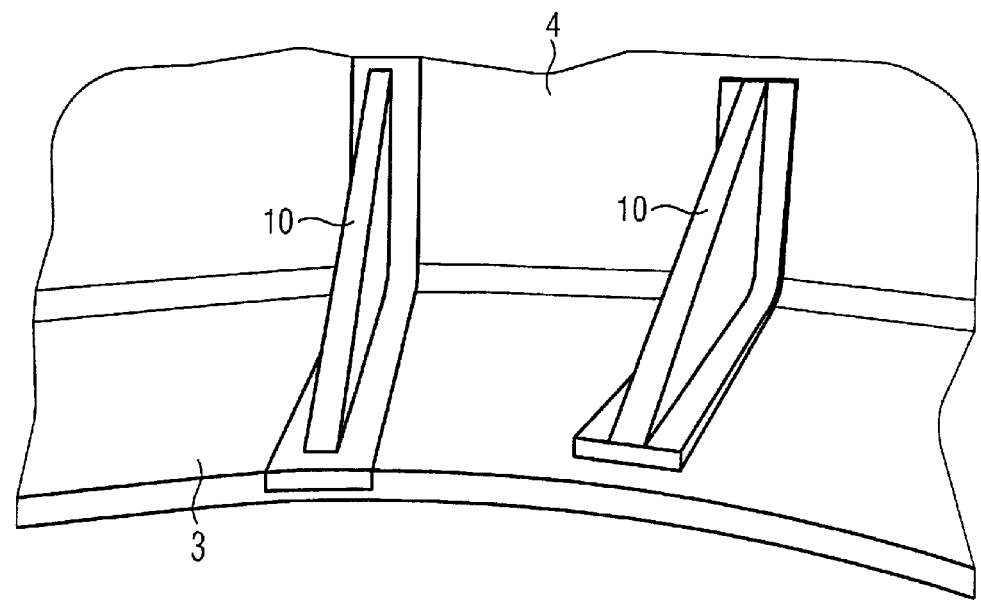
FIG. 4 is a perspective view of a portion of the rotor showing two exemplary embodiments of ribbing of the rotor wall with the retention ring.

A section of the rotor 1 in the transition region between the rotor wall 3 and the retention ring 4 is shown in a perspective view in FIG. 4, wherein the rotor wall 3 and the retention ring 4 are connected with one another by two ribs 10. Two different methods for integration of these ribs 10 are shown as examples in FIG. 4. A rib that was already introduced into the polymer matrix in the manufacture of the rotor wall 3 and the retention ring 4 is shown on the left side. A rib that was merely glued to the two structures is visible on the right side.

Figure 5:
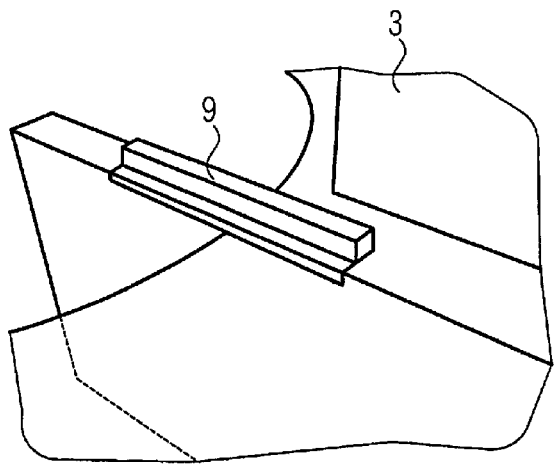
FIG. 5 is a first perspective view of a portion of a retention element integrated into the rotor.
Figure 6:
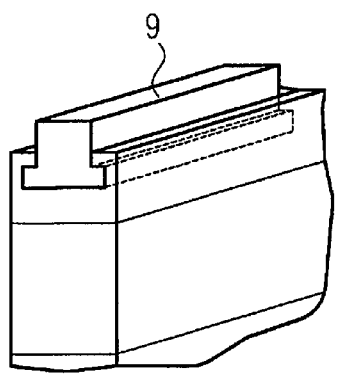
FIG. 6 is a second perspective view of pa portion of the retention element integrated into the rotor.

Moreover, it is possible to introduce additional metal inserts into the polymer matrix in the manufacture, as is shown in two different perspective partial views in FIGS. 5 and 6. The metal inserts can thereby form retention elements 9 to which the components 5, 6 of the acquisition system are attached. Such retention elements 9 can be produced from an aluminum alloy, for example. In this way it is possible that bores are introduced into the retention elements via a machine processing without the structure of the polymer matrix or of the fibers 2 being destroyed. The retention elements 9 can be additionally held via extra textile structures or layer structures of the fibers 2 that are provided in this region. It would likewise be conceivable that the entire composite material is thickened at the positions of the metal inserts. In this way the situation can be allowed for that strong stresses occur at the present spot connections between components 5, 6 and rotor 1.

Figure 7:
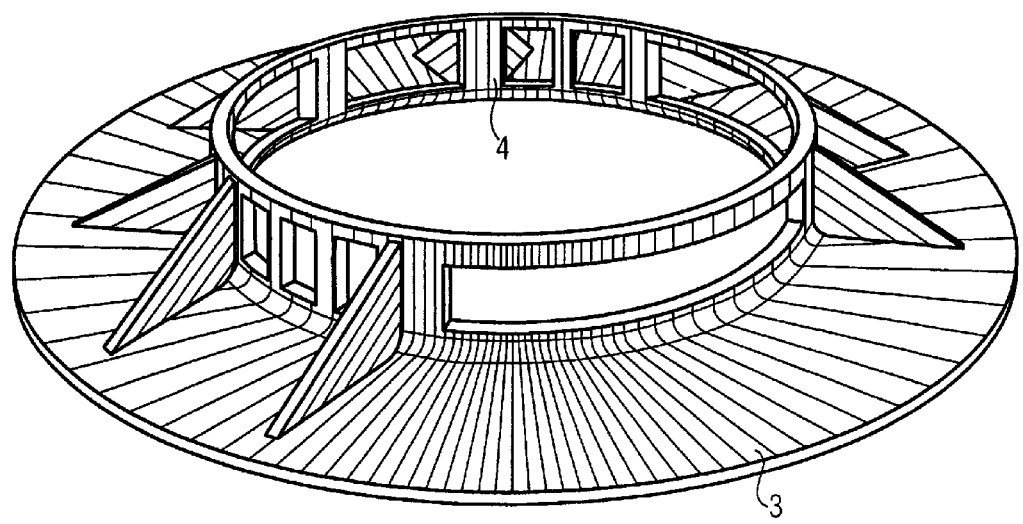
FIG. 7 is a perspective view of a portion of a rotor having, as a rotor wall, a ring rim, on the inner circumference of which are arranged recesses to accommodate components of the acquisition device.

An additional exemplary embodiment of a rotor 1, which is produced from a composite material with polymer matrix reinforced with fibers 2, is shown in FIG. 7. In contrast to the exemplary embodiments already described, the rotor 1 has a rotor wall 3 in the form of a ring rim on whose inner circumference (rather than the outer circumference) is arranged the retention ring 4 for mounting the components 5, 6 of the acquisition device. In this way it is possible to pass a portion of the centrifugal forces near the bearing into the stationary part of the gantry via the retention ring arranged on the inside. A disadvantage of this design is that the components 5, 6 of the gantry are ejected from the region of the gantry due to, for example, a failure of the bolts or via a failure of the material. In the exemplary embodiment in which the retention ring 4 is arranged on the outer circumference of the rotor wall 3, this problem cannot occur since the retention ring 4 simultaneously serves as a protection against ejected parts.

In order to address this risk, the components 5, 6 are pushed through recesses 12 provided for this from the inner radius to the outer radius. The components have an abutment structure by means of which the component 5, 6 can be positively connected with the retention ring 4.

The resin injection method has established itself for the manufacturing of a large-area module such as the rotor 1 in small and medium series. For production the fibers 2 are initially inserted into a work piece; the polymer matrix is subsequently injected into the tool via one opening. Venting takes place through at least on additional opening in the work piece; and curing ensues by heating the composite material. The heating can be done in different ways. In one advantageous form, the heating of the composite material is implemented by a heater integrated into the work piece. As an alternative to this, heating of the composite material can ensue by microwave technology.

In summary, the invention concerns a rotor 1 for a gantry of a computed tomography apparatus, as well as a manufacturing method for such a rotor 1. The rotor 1 according to the invention is produced at least in segments from a composite material with polymer matrix that is reinforced with fibers 2. The rotor 1 thus has a high strength and rigidity, such that the deformation limits to achieve a sufficiently good image quality with simultaneously low structural volume and low weight are not exceeded, even at high rotation speeds.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rotor for a gantry of a computed tomography apparatus comprising:
    a rotor structure configured to mount computed tomography image data acquisition components thereon and configured to rotate around a rotation center; and
    said rotor structure being comprised, at least in segments, of a composite material having a polymer matrix reinforced with fibers.

2. A rotor as claimed in claim 1 wherein said fibers are carbon fibers.

3. A rotor as claimed in claim 1 wherein said fibers are formed as carbon nanotubes.

4. A rotor as claimed in claim 1 wherein said fibers are aligned unidirectionally, at least in segments of said rotor structure, in a direction of force paths that occur upon rotation of said rotor structure.

5. A rotor as claimed in claim 1 wherein said fibers are formed as continuous fibers.

6. A rotor as claimed in claim 1 wherein said fibers form a textile structure, at least in segments of said rotor structure.

7. A rotor as claimed in claim 1 wherein said fibers form a layer structure, at least in segments of said rotor structure.

8. A rotor as claimed in claim 1 wherein said polymer matrix is an epoxy matrix.

9. A rotor as claimed in claim 1 wherein said rotor structure comprises a rotor wall formed by a ring rim and a peripheral retention wall disposed on the outer or inner circumference of said rotor wall, said retention ring being configured to mount said components of said computed tomography image data acquisition device thereon.

10. A rotor as claimed in claim 9 wherein said fibers are oriented radially in said ring rim relative to said rotation center.

11. A rotor as claimed in claim 9 wherein said rotors are directed from said rotor wall to said retention ring, and in said retention ring are oriented parallel to said rotation center.

12. A rotor as claimed in claim 9 wherein said fibers are oriented, in at least one of said rotor wall or said retention ring, in a circumferential direction.

13. A rotor as claimed in claim 9 wherein said rotor wall is supported by ribs.

14. A rotor as claimed in claim 13 wherein said ribs are connected to said retention ring.

15. A rotor as claimed in claim 14 wherein said rotor wall, said retention ring and said ribs are produced as a single, unitary part.

16. A rotor as claimed in claim 14 wherein said rotor wall, said retention ring and said ribs are glued to each other.

17. A rotor as claimed in claim 1 comprising retention elements for mounting said components, said retention elements being integrated into said composite material.

18. A rotor as claimed in claim 17 wherein said rotor structure is thickened with additional fibers in regions thereof at which said retention elements are located.

19. A rotor as claimed in claim 1 wherein said retention elements are comprised of a metal selected from the group consisting of aluminum and aluminum alloys.

20. A rotor as claimed in claim 1 comprising sandwich elements integrated into said composite material.

21. A rotor as claimed in claim 20 wherein each sandwich element is comprised of a plurality of layers of materials with respectively different densities.

22. A computed tomography gantry comprising:
   a stationary frame;
   a rotor rotationally mounted in said stationary frame for rotation around a rotation center;
   a plurality of computed tomography image data acquisition components mounted on said rotor for co-rotation therewith around said rotation center; and
   said rotor comprising a rotor structure comprised, at least in segments, of a composite material with a polymer matrix reinforced with fibers.

23. A method for manufacturing a computed tomography rotor comprising the steps of:
   forming a workpiece in a configuration corresponding to a rotor for a computed tomography apparatus;
   inserting reinforcing fibers into said workpiece;
   injecting a polymer matrix into said workpiece through at least one opening, and venting said workpiece through a further opening therein; and
   curing said workpiece by heating said composite material.

24. A method as claimed in claim 23 comprising heating said composite material by integrating a heating element into said workpiece.

25. A method as claimed in claim 23 comprising heating said composite material using a microwave technology.

* * * * *